(12) United States Patent  (10) Patent No.: US 9,579,015 B2
Henriksen  (45) Date of Patent: Feb. 28, 2017

(54) OPHTHALMIC IMAGE CAPTURE SYSTEMS AND METHODS

(71) Applicant: RSBV, LLC, Fort Collins, CO (US)

(72) Inventor: David Henriksen, Fort Collins, CO (US)

(73) Assignee: RSBV, LLC., Ft. Collins, CO (US)

( * ) Notice: Subject to any disclaimer, the term of this patent is extended or adjusted under 35 U.S.C. 154(b) by 0 days.

(21) Appl. No.: 15/016,834

(22) Filed: Feb. 5, 2016

(65) Prior Publication Data

US 2016/0235288 A1   Aug. 18, 2016

Related U.S. Application Data

(60) Provisional application No. 62/115,744, filed on Feb. 13, 2015.

(51) Int. Cl.
*A61B 3/14* (2006.01)
*A61B 3/00* (2006.01)
*A61B 3/125* (2006.01)
*A61B 3/10* (2006.01)

(52) U.S. Cl.
CPC ............... *A61B 3/0025* (2013.01); *A61B 3/10* (2013.01); *A61B 3/125* (2013.01); *A61B 3/145* (2013.01)

(58) Field of Classification Search
USPC .................................................. 351/200–246
See application file for complete search history.

(56) References Cited

U.S. PATENT DOCUMENTS

| | | | |
|---|---|---|---|
| 8,960,903 B2* | 2/2015 | Horn | A61B 3/102 351/200 |
| 2006/0147189 A1 | 7/2006 | Yogesan | |
| 2008/0292144 A1 | 11/2008 | Kim | |
| 2012/0078241 A1 | 3/2012 | Gooding | |
| 2012/0242957 A1 | 9/2012 | Mordaunt | |

FOREIGN PATENT DOCUMENTS

WO    WO 2013/156999    10/2013

OTHER PUBLICATIONS

International Search Report and Written Opinion dated May 11, 2016 for International Application No. PCT/US2016/016779.

* cited by examiner

*Primary Examiner* — Mohammed Hasan
(74) *Attorney, Agent, or Firm* — Swanson & Bratschun, L.L.C.

(57) ABSTRACT

Apparatus, systems and techniques for capturing, processing and generating digital ophthalmic images using conventional ophthalmic lenses. Certain embodiments processor implemented gesture-based control methods that provide for an eye care specialist to use a gesture-based imaging trigger to capture images of selected ocular structures through a traditional ophthalmic lens.

12 Claims, 12 Drawing Sheets

OPHTHALMIC IMAGE CAPTURE SYSTEMS AND METHODS

RELATED APPLICATIONS

This application claims the benefit under 35 USC section 119 of U.S. provisional application 62/115,744 filed on Feb. 13, 2015 and entitled "Ophthalmic Image Capture Systems and Methods," the content of which is hereby incorporated by reference in its entirety and for all purposes.

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

FIELD

The present disclosure relates, in general, to methods, systems, apparatus, and computer software for capturing ophthalmic images.

BACKGROUND

One aspect of a traditional ophthalmic examination consists of the visual inspection of the patient's retina by an ophthalmologist, optometrist or another trained technician (collectively referred to herein as "eye care specialists"). In many cases, the patient's retina (or other selected ocular structure) is examined by the eye care specialist using a handheld ophthalmic lens. Eye care specialists have therefore become quite comfortable and skilled using handheld lenses as part of their examination routine.

Recently, it has become common for eye care specialists to attempt to take digital photographs of a patient's retina or another ocular structure using a smartphone having a built-in digital camera, or using a video-enabled ophthalmic headset. These ocular images can be taken through specialized imaging lens sets which are attached directly to a phone or video headset using appropriate adapters. Alternatively, retinal images can be captured manually using traditional handheld ophthalmic lenses. In certain instances a traditional ophthalmic lens designed for handheld use can be attached to an imaging device using an adapter. As used herein, the process of capturing a retinal image through a traditional ophthalmic lens designed for handheld use is referred to as the "manual" capture of an image whether or not the ophthalmic lens is actually handheld, or is alternatively connected to the imaging device using an adapter.

During the manual capture process, an eye care specialist might hold a smartphone in one hand and an ophthalmic lens in the other hand. Unfortunately, the requirement to hold the ophthalmic lens and smart phone separately makes it very difficult or impossible to trigger the phone's virtual shutter button using the camera software provided with a typical smart phone. This is true even if the ophthalmic lens is attached to the smart phone using an adapter. In instances where the eye care specialist uses a video-enabled headset, a similar problem may be encountered since the specialist may need to trigger image or video stream capture using the computer keyboard or mouse, while also holding the ophthalmic lens in the proper position with one hand. In summary, it is very difficult for an eye care specialist to manipulate a virtual or real "shutter" button on a smartphone screen, keyboard or mouse while also manipulating the ophthalmic lens into the optimal position for photographing the retina or another ocular structure.

The embodiments disclosed herein are directed toward overcoming one or more of the problems noted above.

BRIEF SUMMARY

Various embodiments disclosed herein include apparatus, systems and techniques for capturing, processing and generating digital ophthalmic images using conventional ophthalmic lenses. In particular, the embodiments described herein include processor implemented "machine vision" like control methods that provide for an eye care specialist to use a gesture-based imaging trigger to capture images of selected ocular structures through a traditional ophthalmic lens. Images may be captured according to the disclosed methods with a smartphone, a video-enabled headset, a video camera, a still camera, a web cam or similar digital image capture apparatus. Each of the foregoing types of imaging apparatus, and similar devices, are referred to herein collectively as "imaging devices."

The disclosed embodiments allow the eye care specialist to trigger an imaging device with a simple gesture. In one disclosed embodiment, the eye care specialist may trigger the capture of an image simply by placing one of their fingertips over a portion of the ophthalmic lens frame. Thus, certain disclosed methods and apparatus create a "soft shutter button" or "virtual shutter button" on the ophthalmic lens frame itself that is enabled purely through image processing methods. This gesture based approach to image capture triggering can be useful as an aid to machine vision based automated capture techniques, or as a standalone approach for triggering individual still shots to be captured during manual video-based ocular examinations.

One particularly disclosed embodiment is a method of capturing a digital ophthalmic image using a system comprising an ophthalmic lens having an ophthalmic lens frame, an imaging device having a digital image sensor and a processor in communication with the imaging device. The processor, and memory storing associated software, may be housed with the imaging device, for example as an application stored in memory and executed by a processor within a smart phone. Alternatively processor, memory and software elements may be housed away from the imaging device, for example as software running on a computer in communication with a video camera.

Method embodiment includes the steps of manually aligning the ophthalmic lens and imaging device with a patient eye to cause an image of a selected eye structure and an image of the ophthalmic lens frame to be focused on the digital image sensor. During the positioning and focusing process, a video stream or other series of preview images may be obtained with the imaging device. The processor executes instructions causing the detection or identification of the ophthalmic lens frame in the video stream data. Subsequently, the processor may detect that a gesture has occurred indicating that the eye care specialist desires to capture a specific image. For example, the processor may detect that a portion of the eye care specialist's finger has obstructed a portion of the ophthalmic lens frame. Upon detecting the gesture, the system can automatically trigger the capture of a desired still frame with the imaging device.

In certain embodiments, the system may further process the captured image. For example the image may be cropped or otherwise processed based upon the detected size and position of the ophthalmic lens frame or another identified region in the captured still image.

Alternative embodiments include systems and apparatus configured to implement the gesture-based image capture methods generally described herein.

Various modifications and additions can be made to the embodiments discussed without departing from the scope of the invention. For example, while the embodiments described above refer to particular features, the scope of this invention also included embodiments having different combination of features and embodiments that do not include all of the above described features.

BRIEF DESCRIPTION OF THE DRAWINGS

A further understanding of the nature and advantages of particular embodiments may be realized by reference to the remaining portions of the specification and the drawings, in which like reference numerals are used to refer to similar components. In some instances, a sub-label is associated with a reference numeral to denote one of multiple similar components. When reference is made to a reference numeral without specification to an existing sub-label, it is intended to refer to all such multiple similar components.

DETAILED DESCRIPTION OF CERTAIN EMBODIMENTS

Figure 1:
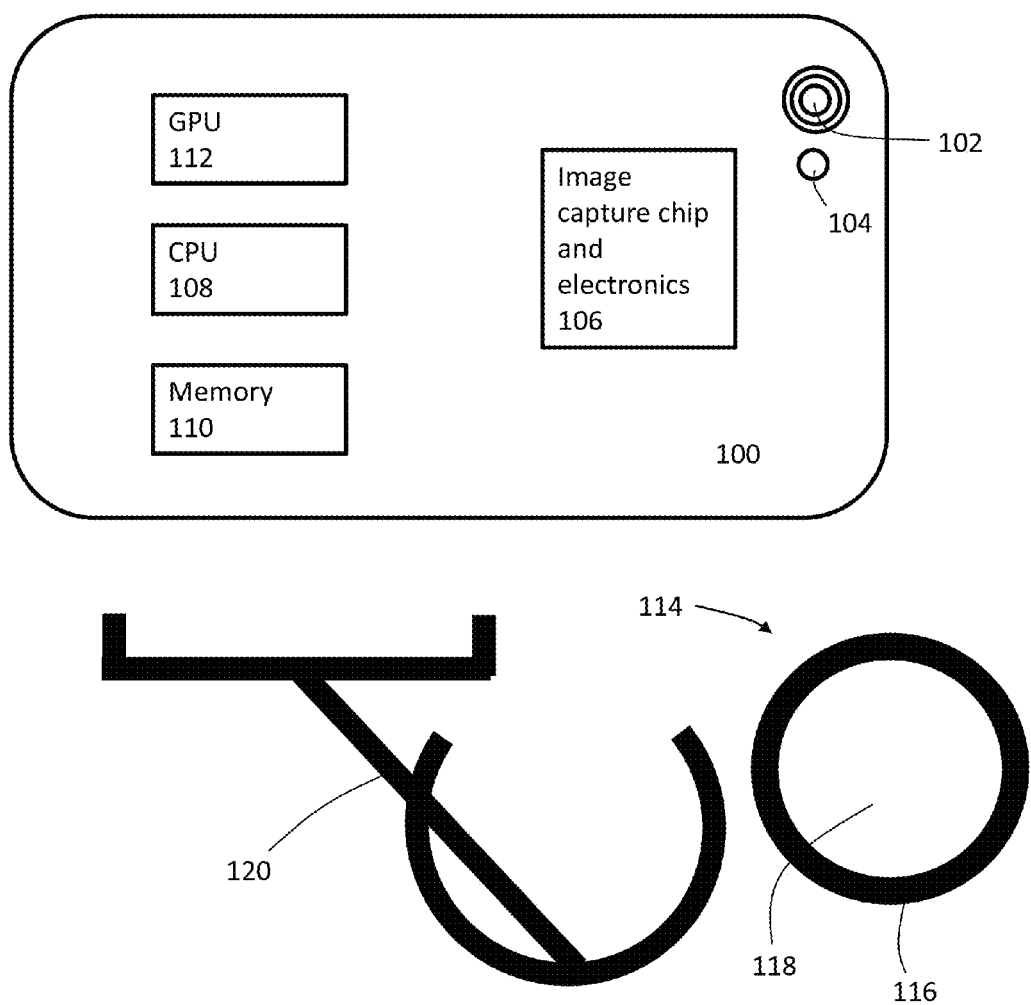
FIG. 1 is a block diagram depiction of a disclosed system embodiment.

While various aspects and features of certain embodiments have been summarized above, the following detailed description illustrates a few exemplary embodiments in further detail to enable one of skill in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present invention may be practiced without some of these specific details. In other instances, certain structures and devices are shown in block diagram form. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

Unless otherwise indicated, all numbers used herein to express quantities, dimensions, and so forth used should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

In general, the embodiments described in this disclosure relate to control methods, systems and apparatus that provide for an eye care specialist to "force capture" one or more selected images of selected ocular structures through a traditional ophthalmic lens. Images may be captured with a smartphone, a video-enabled headset, video camera, a still camera, a web cam, tablet or similar digital imaging apparatus. Each of the foregoing types of imaging apparatus, and similar devices, are referred to herein collectively as "imaging devices."

The disclosed embodiments allow the eye care specialist to trigger an imaging device to capture an image with a simple gesture that is detected by the system. For example, in one specifically disclosed embodiment, the eye care specialist may trigger the capture of an image simply by placing one of their fingertips over a portion of the ophthalmic lens frame. The methods and apparatus disclosed herein could be implemented with other alternative gestures being detected by the system causing the triggering of an image capture. Suitable gestures will be easily and conveniently performed while the eye care specialist is holding an imaging device and/or ophthalmic lens in the proper spatial relationship to a patient eye.

As noted above, one gesture which is particularly well suited to the capture of ophthalmic images is the placement of a portion of one or more of the specialist's fingers over a portion of the ophthalmic lens frame. Thus, the specifically disclosed methods and apparatus create a "soft shutter button" or "virtual shutter button" on the ophthalmic lens frame itself which is enabled purely through image processing methods. This gesture based approach to image capture triggering can be useful as an aid to machine vision based automated capture techniques, or as a standalone approach for triggering individual still shots to be captured during manual video-based occular examinations.

Accordingly, as shown in FIG. 1 apparatus and system embodiments will include an imaging device 100. The particular imaging device 100 illustrated in FIG. 1 is a smart phone configured to capture still images and/or a stream of video frames. Accordingly, the imaging device 100 includes a lens 102, an illumination source 104, and internal hardware and software including but not limited to an imaging chip and associated electronics 106, a central processing unit (CPU) 108 and memory 110. In certain embodiments the imaging device 100 may include a graphics processing unit (GPU) 112.

Although the imaging device 100 illustrated on FIG. 1 is represented as a smart phone with imaging capabilities, it is important to recognize that the embodiments disclosed herein are not limited to smart phone embodiments. In particular, the imaging device can be any type of camera, video camera, tablet, web cam or other device configured to capture digital still or video images. In addition, certain elements such as memory 110, and CPU 108 may be located in an outboard device, a computer for example, which is in communication with the imaging device 100.

Returning to FIG. 1, system embodiments also include an ophthalmic lens 114. The ophthalmic lens includes a frame 116 surrounding a transparent glass or plastic refractive lens elements 118. During visual examinations, the ophthalmic lens 114 is hand-held by an eye care specialist to assist with the inspection of internal ocular structures, the retina for example. During handheld use, the ophthalmic lens 114 is grasped by the frame 116 as described in detail below. Many ophthalmic lenses 114 are round and are therefore feature round frames 116 as illustrated in FIG. 1. The scope of the present disclosure includes ophthalmic lenses 114 having frames 116 which are of other shapes.

As noted above, an ophthalmic lens 114 is traditionally handheld by an eye care specialist. In certain embodiments disclosed herein, an optional adapter 120 is provided to connect the ophthalmic lens 114 to the imaging device 100 for use. Although an adapter 120 may be used to position the ophthalmic lens 114 with respect to the imaging device 100, the eye care specialist will still be required to manually position the imaging device/adapter/ophthalmic lens assembly with respect to the patient's eye.

The proper distances between the patient eye and the ophthalmic lens and between the ophthalmic lens and the lens of the imaging device are determined by the optical parameters of the ophthalmic lens and imaging lens. In use, these distances may be adjusted independently or together to a spatial relationship where an image of the selected structure of the patient's eye is substantially focused on the imaging chip 106 of the imaging device.

In certain embodiments, the eye care specialist may be observing a video preview on a screen or monitor, for example a smart phone screen opposite the smart phone lens 102, to assist with proper imaging device 100 and ophthalmic lens 114 placement and positioning.

In certain embodiments, an on-board light source, for example the smart phone illumination source 104 of FIG. 1 may be used to illuminate internal or external structures of the patient's eye during the disclosed image capture processes. In other embodiments an external light source or no light source may be utilized.

Figure 2:
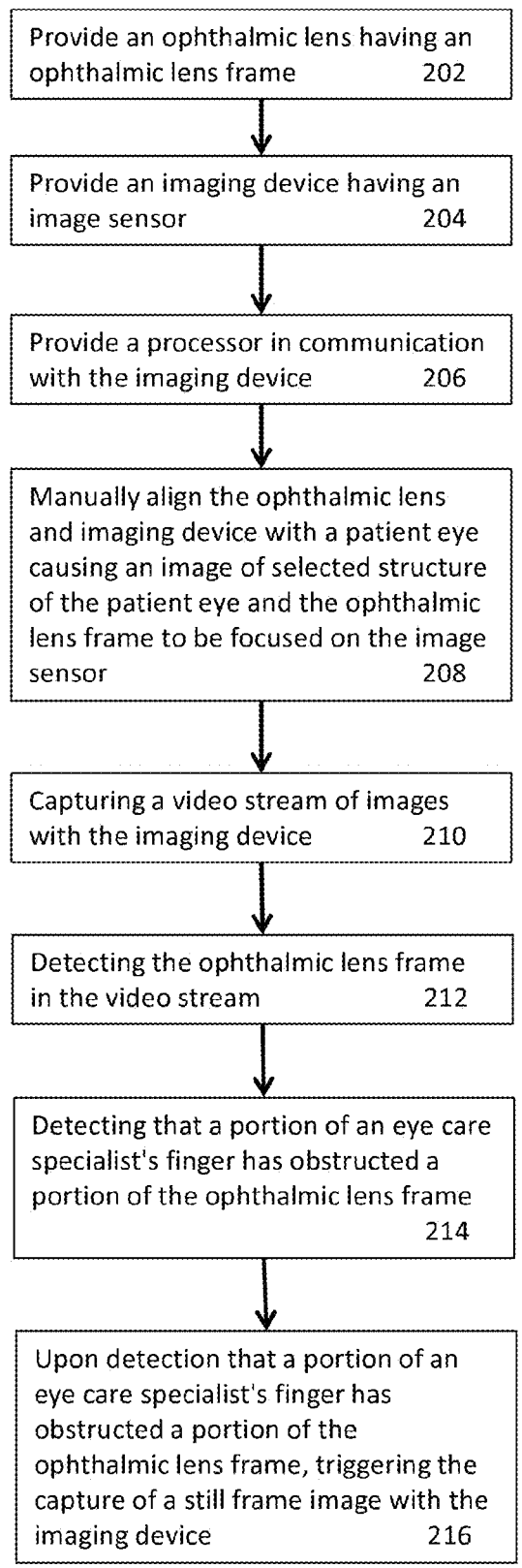
FIG. 2 is a is a general schematic flow diagram depiction of a method as disclosed herein

As described on FIG. 2, certain embodiments disclosed herein are gesture-based methods of triggering the capture of one or more ophthalmic images using the above described or similar apparatus. In particular, method embodiments include the steps of providing an ophthalmic lens having an ophthalmic lens frame, providing an imaging device having an image sensor and providing a processor in communication with the imaging device (Steps 202, 204 and 206 of FIG. 2).

Figure 3:
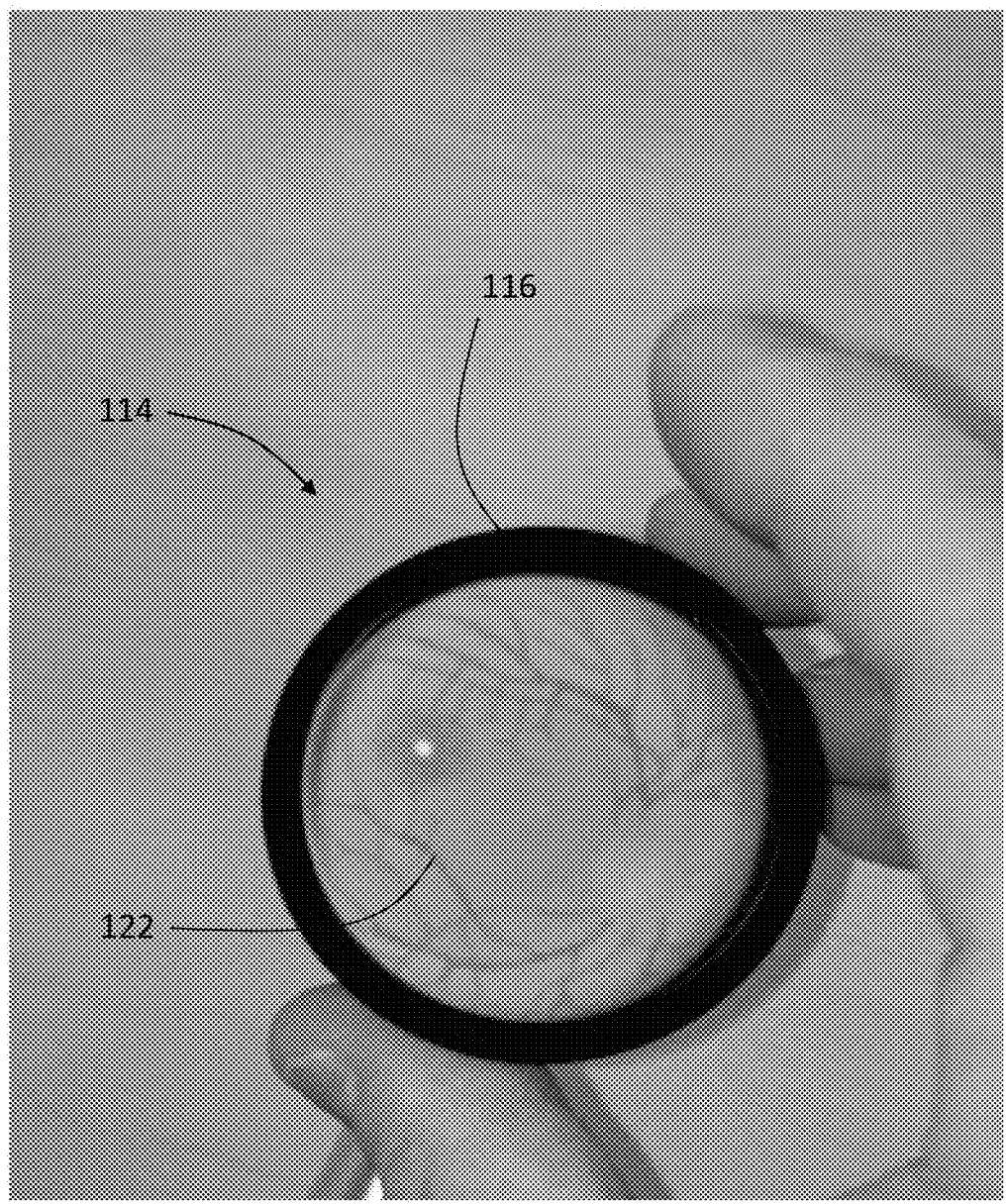
FIG. 3 is an illustration of a fully hand-held system embodiment positioned for use, but before an image is captured.

Using this, or similar apparatus, the eye care specialist manually aligns the ophthalmic lens and imaging device with the patient eye causing an image of selected ocular structure(s) and an image of the ophthalmic lens frame 116 to be focused on the image sensor (step 208). As noted above, the eye care specialist may use a video preview mode of a smart phone or other video enabled imaging device 100 to assist with this step. FIG. 3 illustrates one embodiment of a system as disclosed herein with all elements positioned as appropriate during Step 208. In particular, FIG. 3 shows an ophthalmic lens 114 having a frame 116 handheld by an eye care specialist. The FIGS. 3-12 images were obtained using a synthetic eye model that is useful for simulating retinal image acquisition. Accordingly FIG. 3 also shows an image of a simulated retina 122 as would be viewed by the eye care specialist in a video preview mode.

Figure 4:
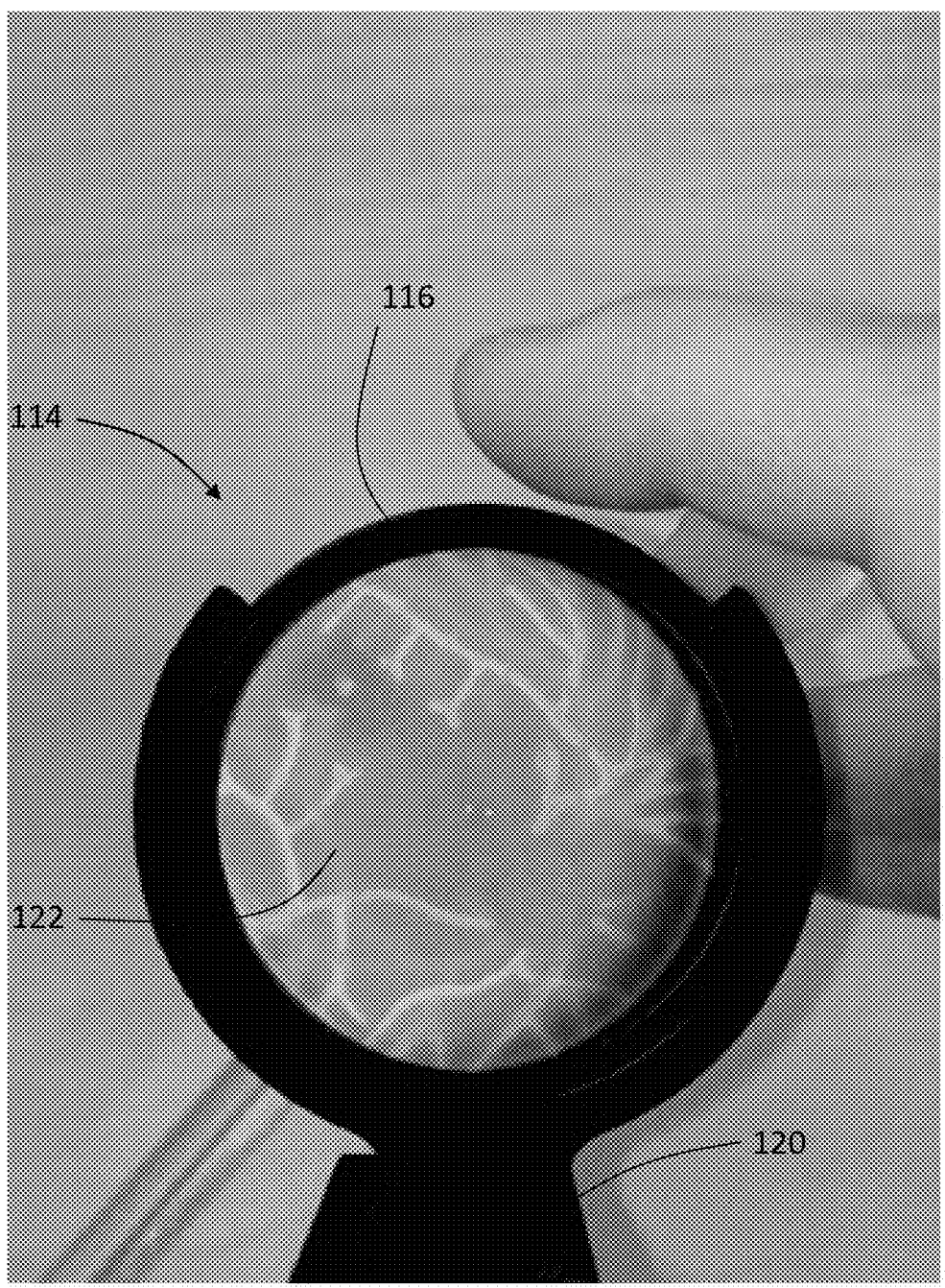
FIG. 4 is an illustration of an alternative system embodiment featuring an adapter between the imaging device and ophthalmic lens, positioned for use, but before an image is captured.

FIG. 4 also illustrates a system configured and positioned at the point in time of Step 208. In the FIG. 4 embodiment, however, the ophthalmic lens 114 is supported by and connected to the imaging device 100 by an adapter 120. Whether or not an adapter 120 is utilized, the eye care specialist must appropriately position the ophthalmic lens 114 with respect to the patient's eye. Accordingly, embodiments featuring a handheld ophthalmic lens 114 and embodiments featuring an adapter 120 are both variations of a manually positioned ophthalmic lens.

Upon the proper positioning of both the ophthalmic lens 114 and the imaging device 100, software associated with a processor, for example CPU 108, is utilized to identify the location and relative size of the ophthalmic lens frame 116 in image data (Steps 210 and 212). Data associated with each image of a preview video stream may be examined by the processor, or data associated with selected images from a preview video stream or other series of images may be examined. In either embodiment, the real-time size and location of the ophthalmic lens frame 116 is identified by the processor in the image data. Because of the relatively small size of ophthalmic lenses, the image sensor on the imaging device 100 will typically have a field of view that extends beyond the region of the ophthalmic lens frame 116.

Figure 5:
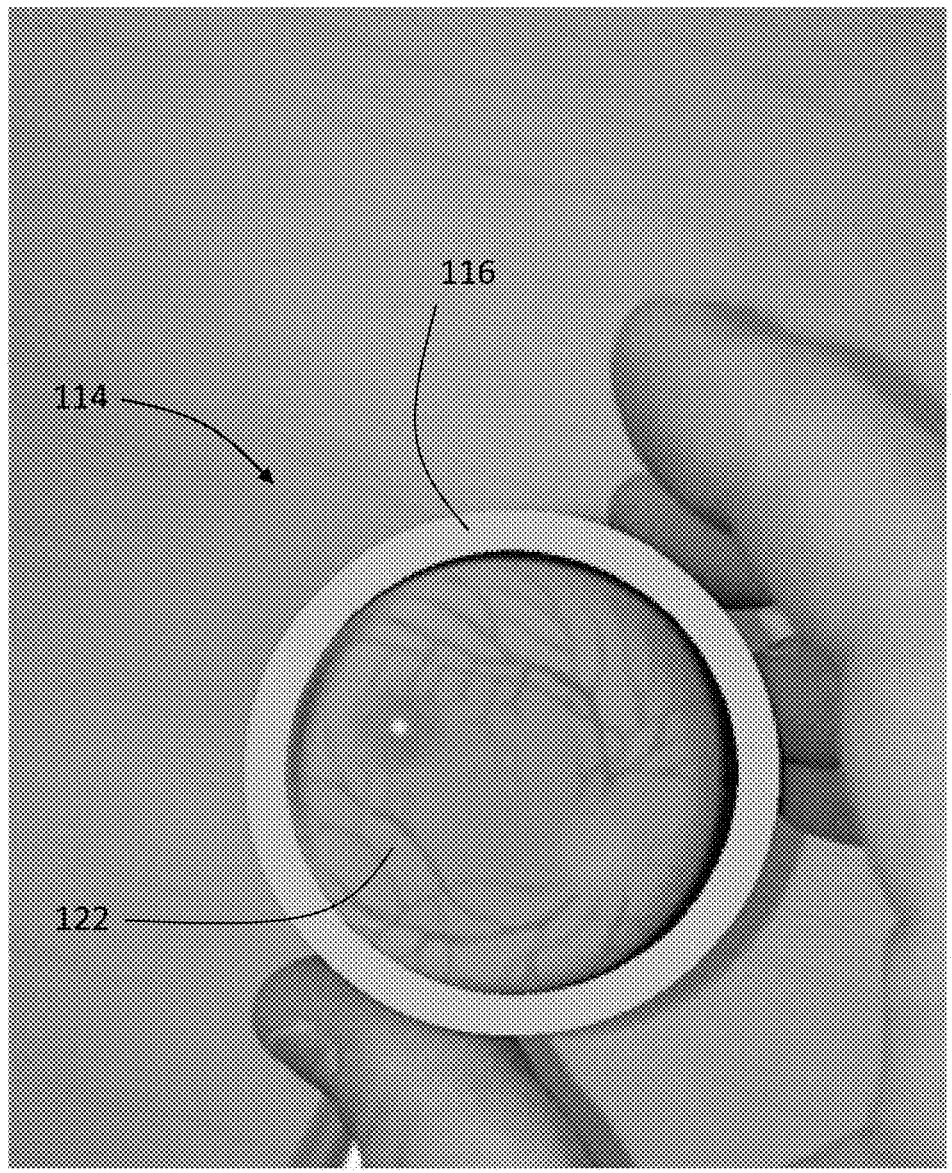
FIG. 5 is an illustration of the FIG. 3 embodiment showing the identification of the ophthalmic lens frame by the processor on a preview image frame.
Figure 6:
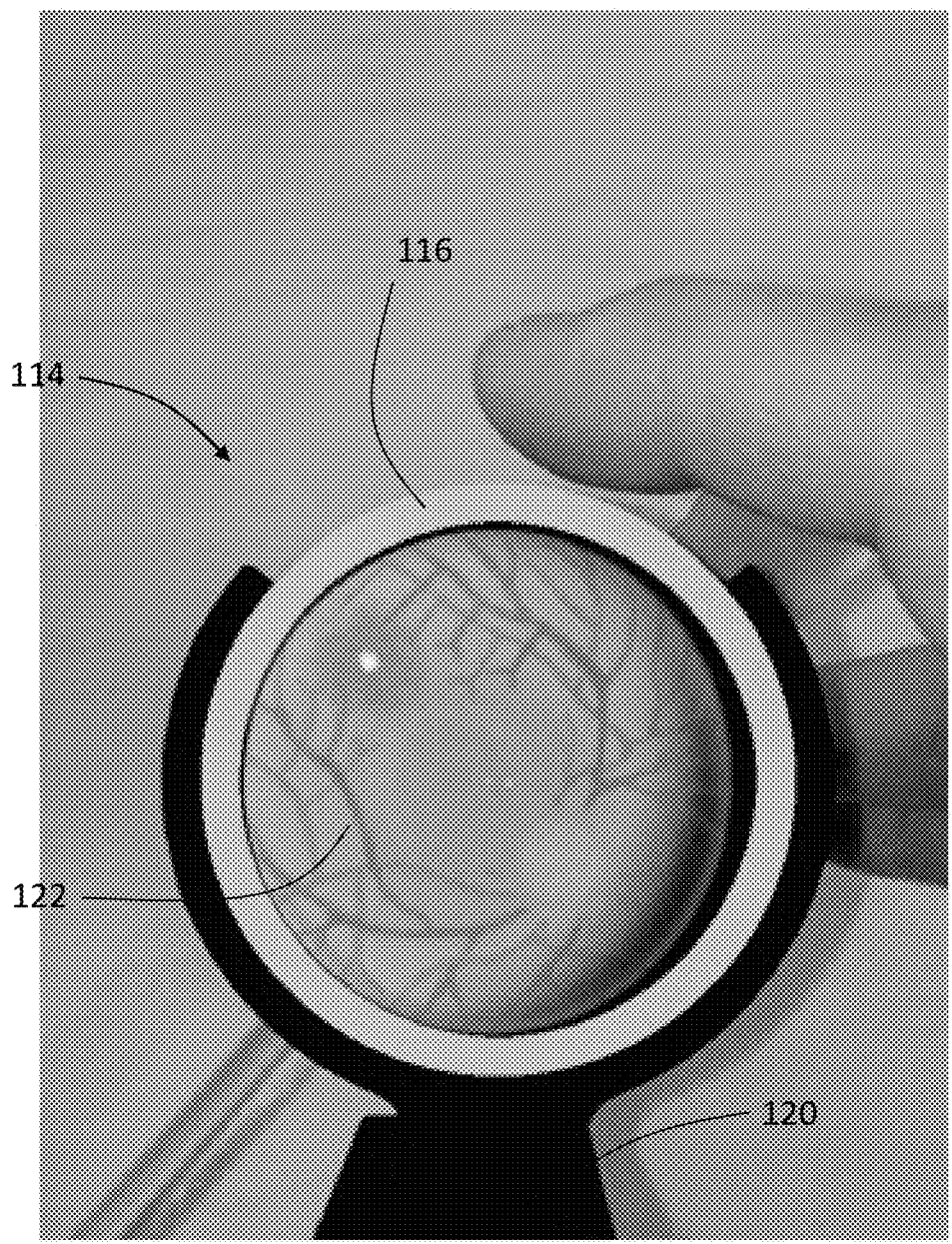
FIG. 6 is an illustration of the FIG. 4 embodiment showing the identification of the ophthalmic lens frame by the processor on a preview image frame.

The process of determining the location and relative size of the circular ophthalmic lens frame 116 within the source image or source video stream data can be performed using one or more of a wide variety of machine vision, software-based, object detection techniques. In the illustrated examples, software executed by a processor, for example CPU 108 may provide for the detection of ring shaped objects within the image data. Among the simplest of techniques for detecting a ring shaped object is to apply ring shaped image masks having varying sizes and locations to the entire source image data on a frame-by-frame basis or to selected frames, to identify a mask size and location that yields a most likely match for the ophthalmic lens frame 116. The images of FIGS. 5-6 illustrate handheld and adapter-based embodiments at the point in time of Step 212, where the size and location of the ophthalmic lens frame 116 has been detected in image data.

Figure 7:
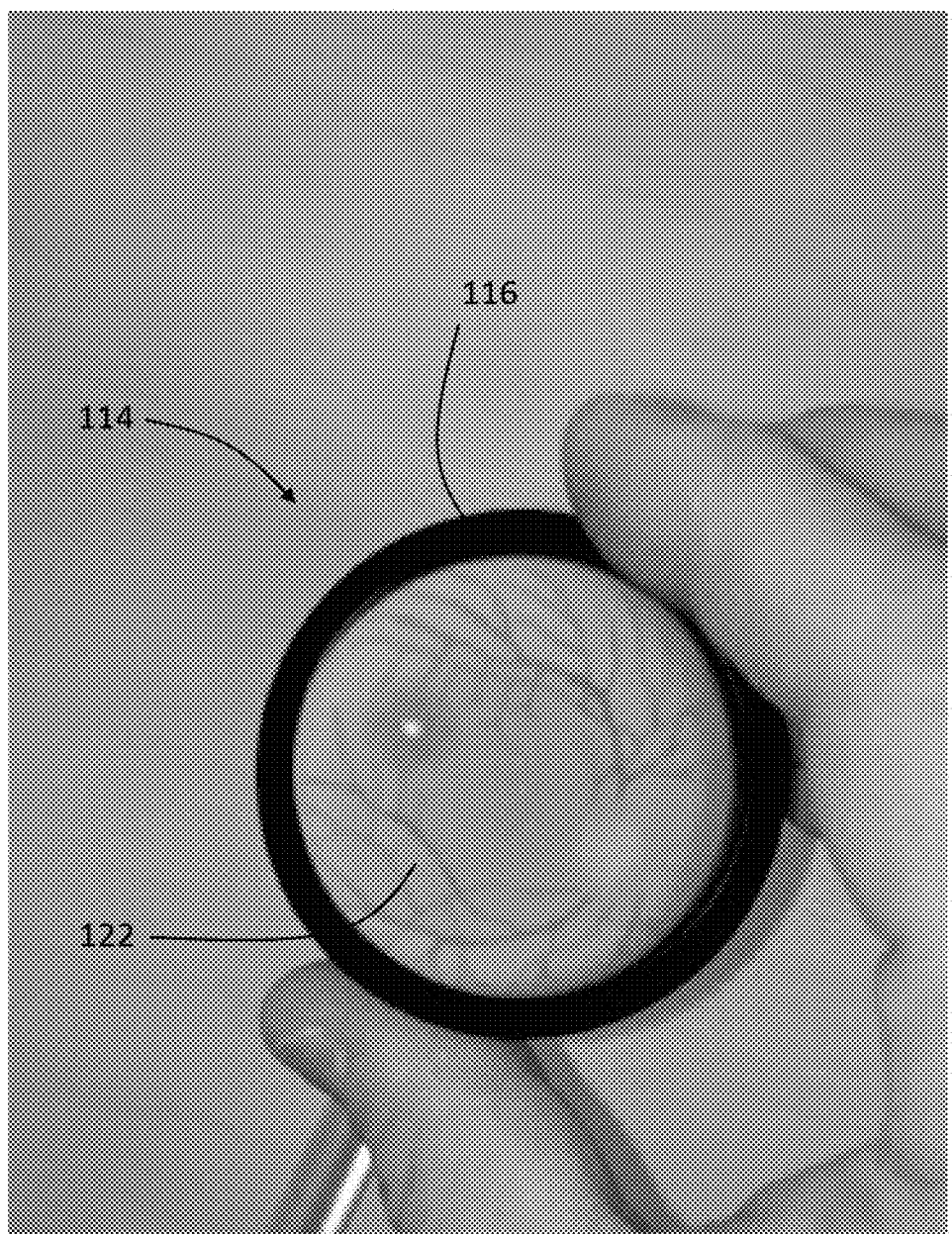
FIG. 7 is an illustration of the FIG. 3 embodiment showing a gesture, in particular the positioning of an eye care specialist's finger across a portion of the ophthalmic lens frame indicating that the specialist desires to capture an image.
Figure 8:
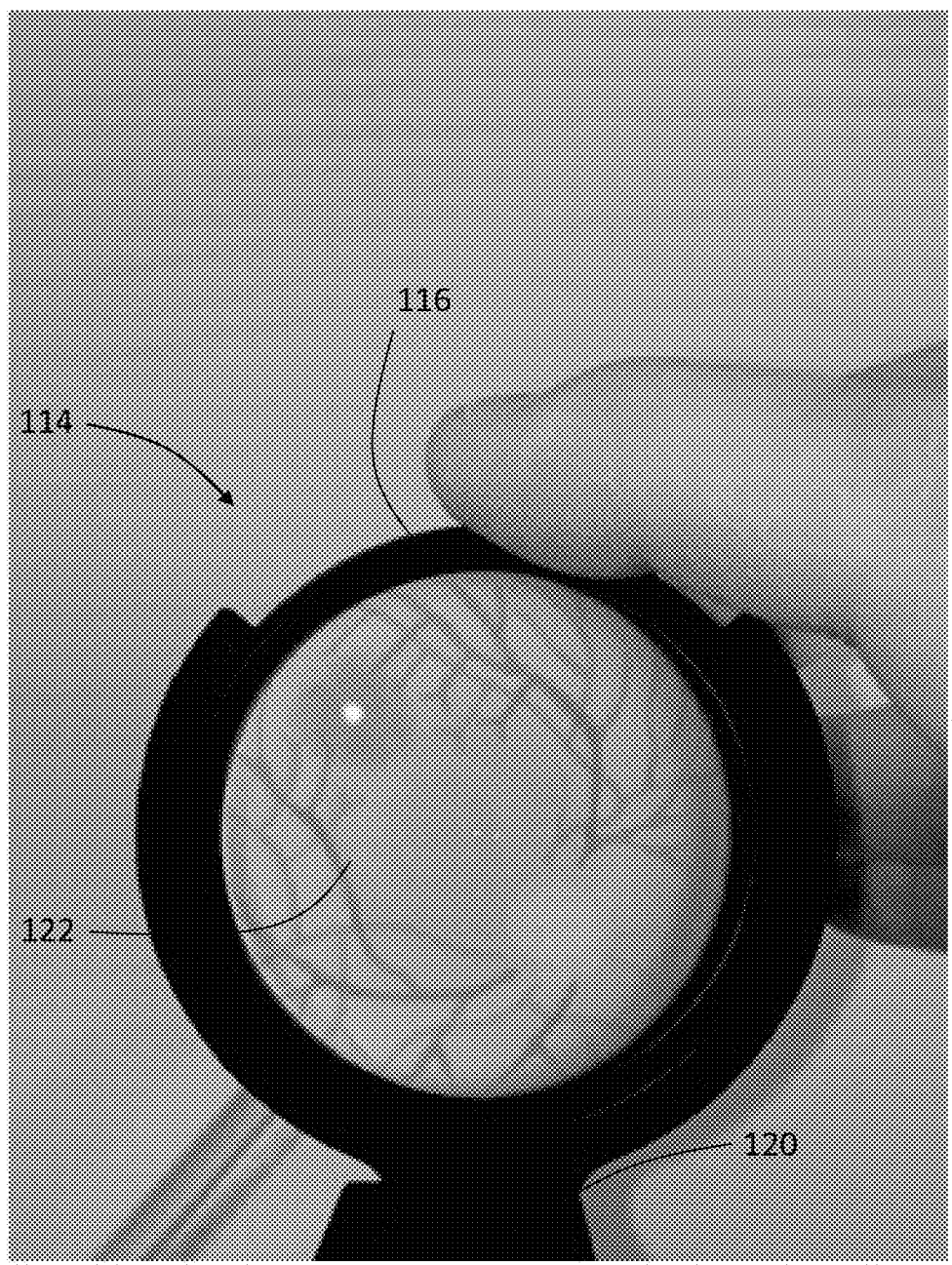
FIG. 8 is an illustration of the FIG. 4 embodiment showing a gesture, in particular the positioning of an eye care specialist's finger across a portion of the ophthalmic lens frame indicating that the specialist desires to capture an image.

As noted above, the capture of a specific image is triggered by the eye care specialist when he or she makes a pre-determined gesture, for example placing one of their fingertips over a portion of the ophthalmic lens frame 116. Thus, certain disclosed methods and apparatus create a "soft shutter button" or "virtual shutter button" on the ophthalmic lens frame 116 that is enabled purely through image processing methods. Accordingly, after the system has detected the ophthalmic lens frame in video stream data (or in the data of selected images) the processor may be used to determine if any portion (or a selected portion) of the identified ophthalmic lens frame becomes obstructed by a portion of the eye care specialist's finger (Step 214). The images of FIGS. 7-8 illustrate various system embodiments at the point in time of Step 214, where the ophthalmic lens frame 116 is partially obstructed by the eye care specialist's finger.

Various software routines may be utilized to detect in real time, within the image data, that an eye care specialist's finger is obstructing a portion of the ophthalmic lens frame 116. For example, one method includes counting the number of pixels within the data previously identified as showing the region of the ophthalmic lens frame 116. The number of pixels determined to be within the image of the ophthalmic lens frame 116 may be determined by counting pixels having a color, intensity or other attribute utilized in Step 212 to identify the ophthalmic lens frame within selected image data. Then, pixels which show a color variance, intensity variance or other attribute variance when compared to the pixels associated with the ophthalmic lens frame can be detected, thereby causing the processor to determine that the eye care specialist's finger is partially obstructing the ophthalmic lens frame and indicating that a still shot of the retina or other ocular structure should be captured (Step 216).

Figure 9:
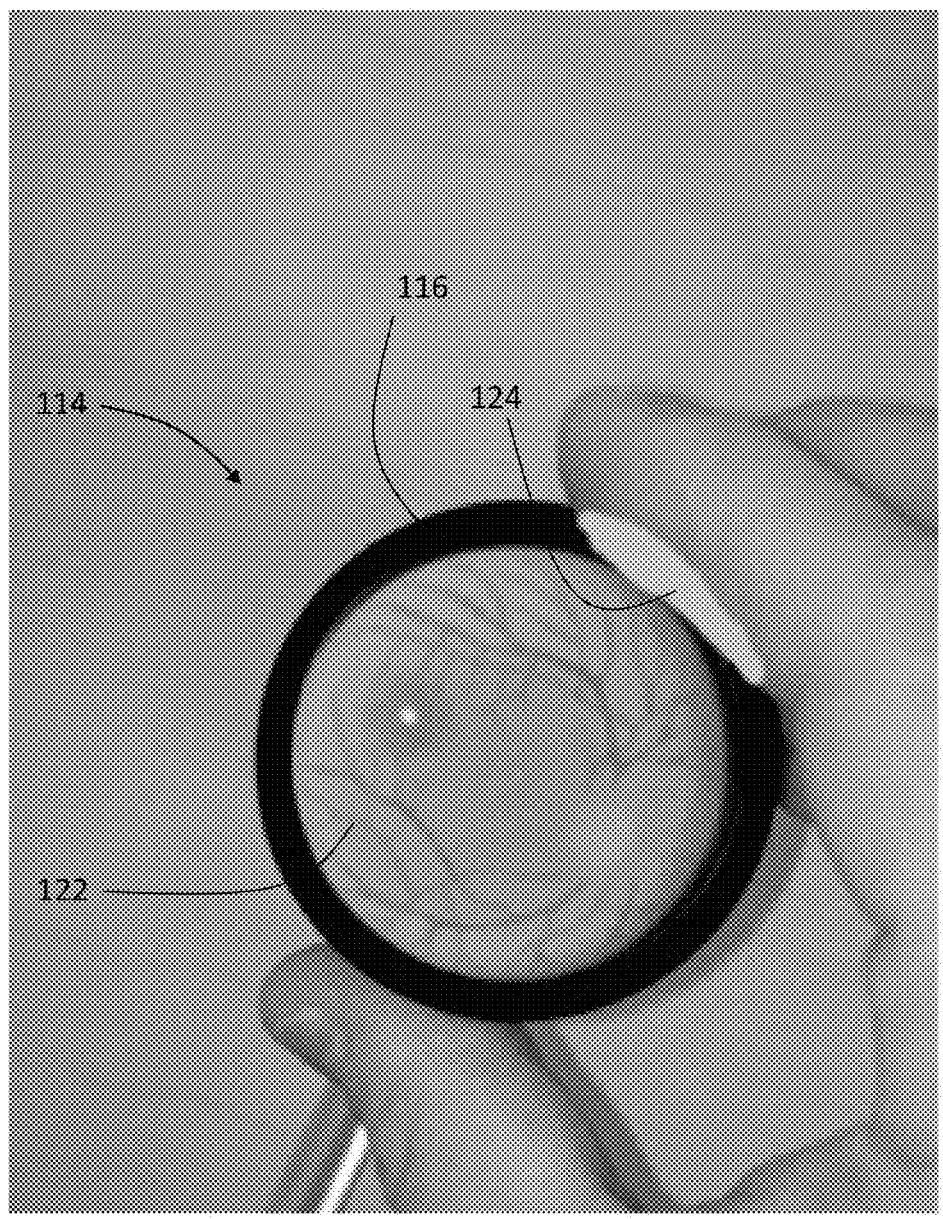
FIG. 9 is the image of FIG. 7 with certain pixels highlighted to illustrate detection by the system that a portion of the ophthalmic lens frame is obstructed by the eye care specialist's finger.
Figure 10:
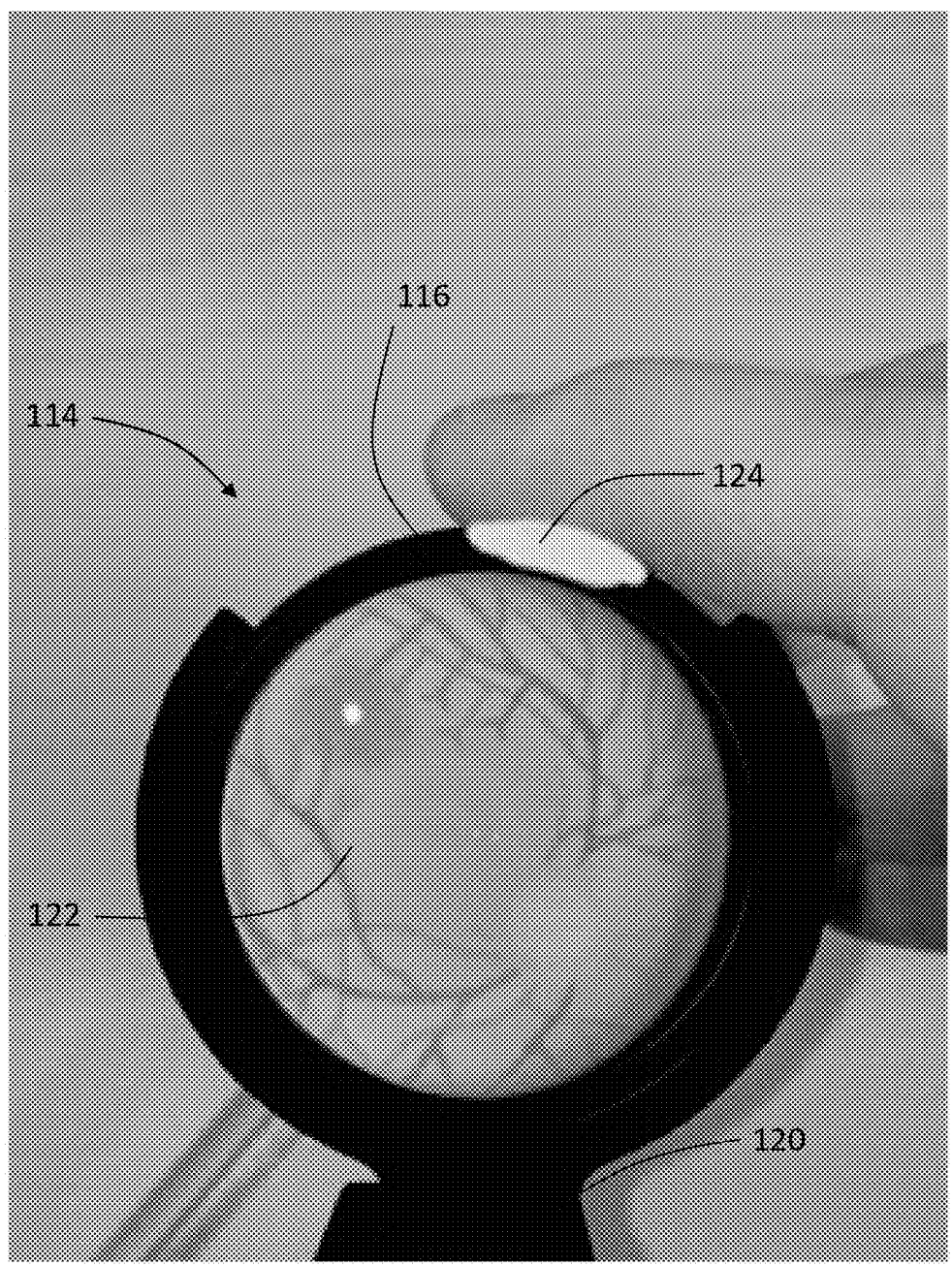
FIG. 10 is the image of FIG. 8 with certain pixels highlighted to illustrate detection by the system that a portion of the ophthalmic lens frame is obstructed by the eye care specialist's finger

The images of FIGS. 9-10 depict areas within image data previously identified as corresponding to the ophthalmic lens frame which now contain a significant color or intensity variance compared to the average color or intensity of the ophthalmic lens frame data. The highlighted color portions 124 are therefore interpreted by the processor as showing that a portion of the lens frame that has been obstructed by the eye care specialist's finger.

In a more specific, but nonlimiting embodiment, the processor may be configured to determine that an image triggering gesture has occurred if the number of pixels that exceed a pre-determined color or intensity variance within the identified ophthalmic lens frame image exceeds a given total pixel count. Upon detection of this threshold, the software/processor will have determined that the eye care specialist desires to capture an image of a selected ocular structure. The imaging device 100 may then be triggered and controlled to capture the desired image.

Figure 11:
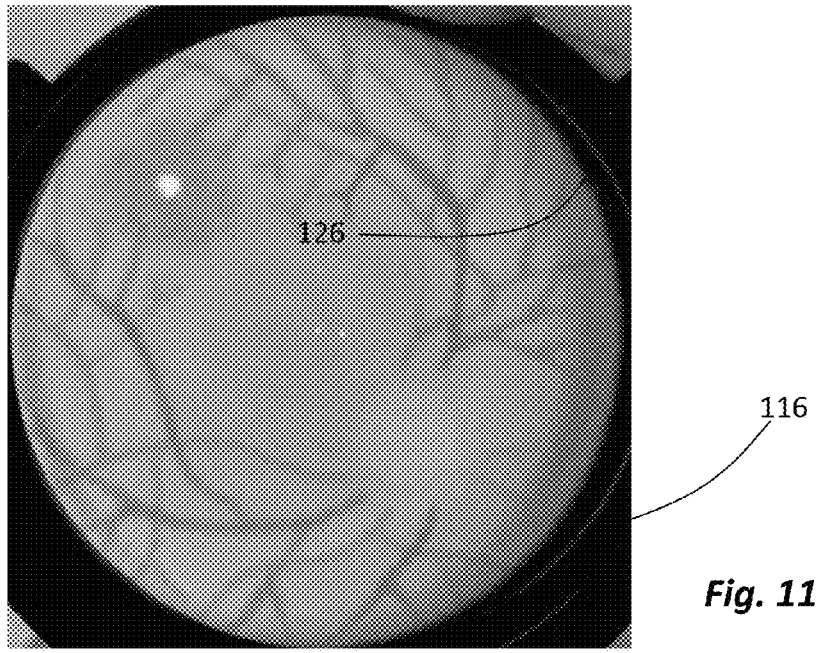
FIG. 11 is a captured and cropped image obtained by disclosed system and method embodiments.
Figure 12:
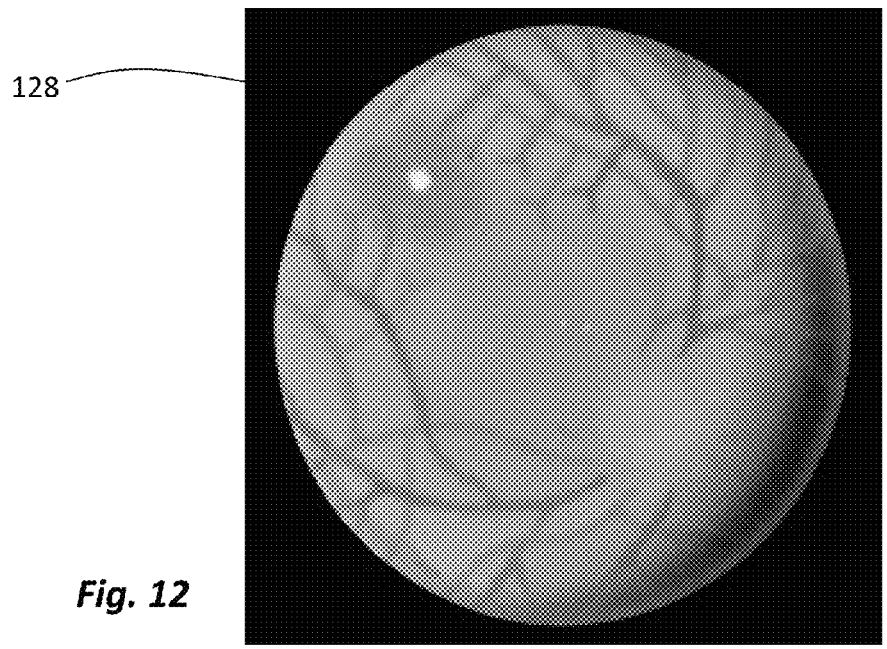
FIG. 12 is the image of FIG. 11 featuring an optional solid-colored synthetic iris generated by the disclosed system and method embodiments.

In addition, because the system has already identified the relative size and location of the ophthalmic lens frame on the image capture chip, the software and processor can optionally, as shown in FIG. 11, crop the captured image so that it only contains the portion of the captured image that falls within a pre-set limit, for example within the inner boundary 126 of the identified ophthalmic lens frame 116. Furthermore, as shown in FIG. 12, the system may optionally create a synthetic iris 128 along the outside of the pre-set limit and fill the synthetic iris, with a given solid color.

In certain alternative embodiments it may be beneficial implement Steps 212-216 with respect to only a pre-determined portion of the ophthalmic lens frame such as the top, left, right, or bottom areas to determine if the eye care specialist's finger has partially obstructed the ophthalmic lens frame. Thus, in some situations it may be beneficial to only create gesture based soft capture buttons on a portion of the ophthalmic lens frame. This alternative would give the eye care specialist the rest of the ophthalmic lens frame to be used for holding the lens without inadvertently triggering a gesture based capture of the image.

As noted above, one apparatus embodiment includes a smartphone imaging device 100 having CPU 108, memory 110 and other architecture providing for the implementation of the described methods. Alternative embodiments may include a dedicated still or video camera or other imaging device communicating with a computer of any type which may include software configured to implement the foregoing methods.

Figure 13:
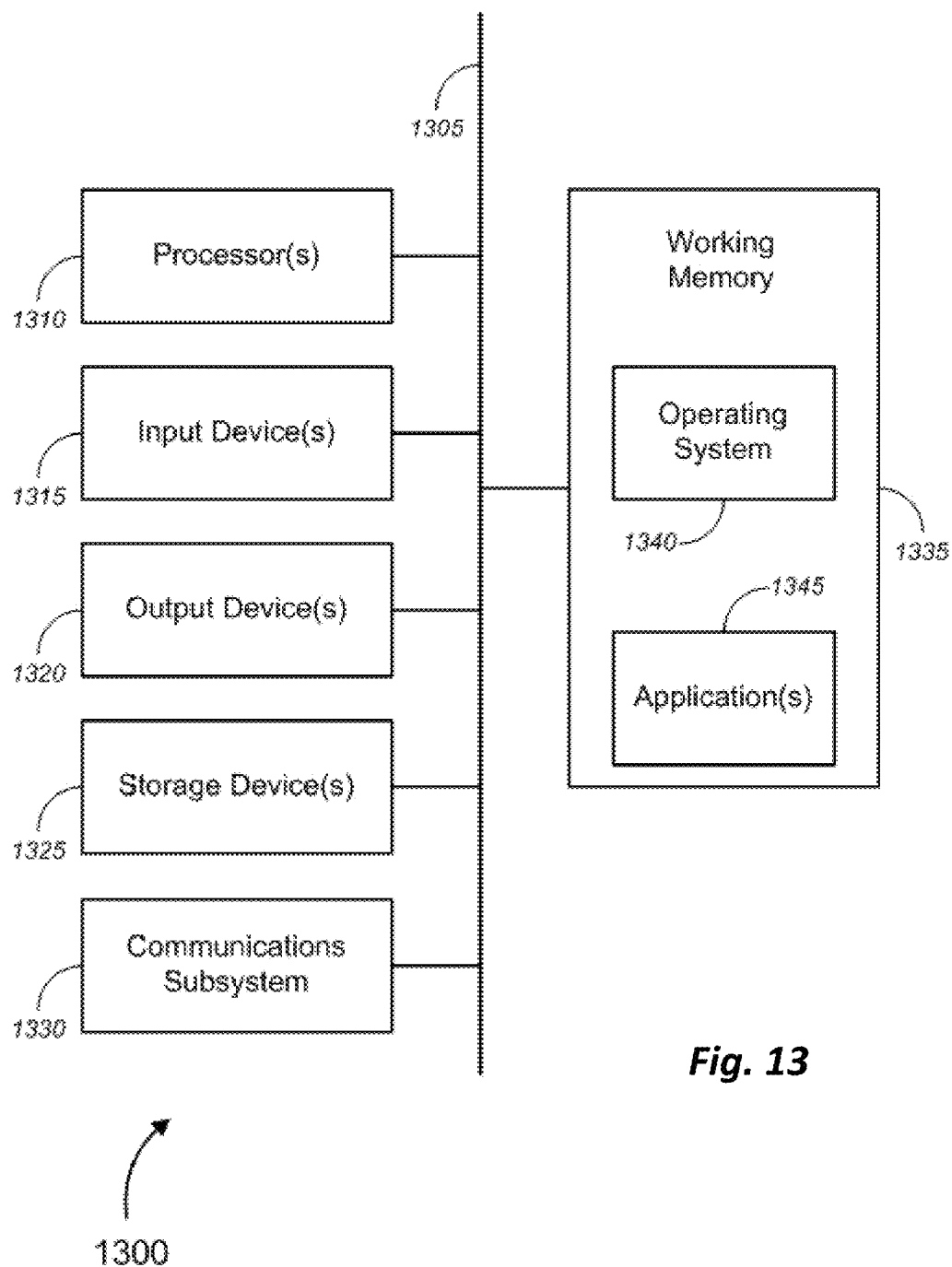
FIG. 13 is a block diagram illustrating an exemplary computer architecture, in accordance with selected embodiments

FIG. 13 is a block diagram illustrating an exemplary computer architecture. FIG. 13 provides a schematic illustration of one embodiment of a computer system 1300 that can perform the methods provided by various other embodiments, as described herein. It should be noted that FIG. 13 is meant only to provide a generalized illustration of various components, of which one or more, or none, of each may be utilized as appropriate. FIG. 13, therefore, broadly illustrates how individual system elements may be implemented in a relatively separated or relatively more integrated manner.

The computer system 1300 is shown comprising hardware elements that can be electrically coupled via a bus 1305, or may otherwise be in communication, as appropriate. The hardware elements may include one or more processors 1310, including without limitation one or more general-purpose processors, or one or more special-purpose processors such as digital signal processing chips, graphics acceleration processors, or the like; one or more input devices 1315, which can include without limitation a mouse, a keyboard, or the like; and one or more output devices 1320, which can include without limitation a display device, a printer, or the like.

The computer system 1300 may further include, or be in communication with, one or more storage devices 1325. The one or more storage devices 1325 can comprise, without limitation, local and/or network accessible storage, or can include, without limitation, a disk drive, a drive array, an optical storage device, a solid-state storage device. The solid-state storage device can include, but is not limited to, one or more of a random access memory ("RAM") or a read-only memory ("ROM"), which can be programmable, flash-updateable, or the like. Such storage devices may be configured to implement any appropriate data stores, including without limitation various file systems, database structures, or the like.

The computer system 1300 might also include a communications subsystem 1330, which can include without limitation a modem, a network card (wireless or wired), an infra-red communication device, a wireless communication device or chipset, or the like. The wireless communication device might include, but is not limited to, a Bluetooth™ device, an 802.11 device, a WiFi device, a WiMax device, a WWAN device, cellular communication facilities, or the like.

The communications subsystem 1330 may permit data to be exchanged with a network, with other computer systems, with any other devices described herein, or with any combination of network, systems, and devices. According to some embodiments, a network might include a local area network ("LAN"), including without limitation a fiber network, an Ethernet network, a Token-Ring™ network, and the like; a wide-area network ("WAN"); a wireless wide area network ("WWAN"); a virtual network, such as a virtual private network ("VPN"); the Internet; an intranet; an extranet; a public switched telephone network ("PSTN"); an infra-red network; a wireless network, including without limitation a network operating under any of the IEEE 802.11 suite of protocols, the Bluetooth™ protocol, or any other wireless protocol; or any combination of these or other networks. In many embodiments, the computer system 1300 will further comprise a working memory 1335, which can include a RAM or ROM device, as described above.

The computer system 1300 may also comprise software elements, shown as being currently located within the working memory 1335, including an operating system 1340, device drivers, executable libraries, or other code. The software elements may include one or more application programs 1345, which may comprise computer programs provided by various embodiments, or may be designed to implement methods and/or configure systems provided by other embodiments, as described herein. Merely by way of example, one or more procedures described with respect to the methods discussed above might be implemented as code or instructions executable by a computer or by a processor within a computer. In an aspect, such code or instructions can be used to configure or adapt a general purpose computer, or other device, to perform one or more operations in accordance with the described methods.

A set of these instructions or code might be encoded and/or stored on a non-transitory computer readable storage medium, such as the storage devices 1325 described above. In some cases, the storage medium might be incorporated within a computer system, such as the system 1300. In other embodiments, the storage medium might be separate from a computer system—that is, a removable medium, such as a compact disc, or the like. In some embodiments, the storage medium might be provided in an installation package, such that the storage medium can be used to program, configure, and/or adapt a general purpose computer with the instructions/code stored thereon. These instructions might take the form of executable code, which is executable by the computer system 1300, or might take the form of source or installable code. The source or installable code, upon compilation, installation, or both compilation and installation, on the computer system 1300 might take the form of executable code. Compilation or installation might be performed using any of a variety of generally available compilers, installation programs, compression/decompression utilities, or the like.

It will be apparent to those skilled in the art that substantial variations may be made in accordance with specific requirements. For example, customized hardware—such as programmable logic controllers, field-programmable gate arrays, application-specific integrated circuits, or the like—might also be used. In some cases, particular elements might be implemented in hardware, software (including portable software, such as applets, etc.), or both. Further, connection to other computing devices such as network input/output devices may be employed.

As mentioned above, in one aspect, some embodiments may employ a computer system, such as the computer system 1300, to perform methods in accordance with various embodiments of the invention. According to a set of embodiments, some or all of the procedures of such methods might be performed by the computer system 1300 in response to processor 1310 executing one or more sequences of one or more instructions. The one or more instructions might be incorporated into the operating system 1340 or other code that may be contained in the working memory 1335, such as an application program 1345. Such instructions may be read into the working memory 1335 from another computer readable medium, such as one or more of the storage devices 1325. Merely by way of example, execution of the sequences of instructions contained in the working memory 1335 might cause the one or more processors 1310 to perform one or more procedures of the methods described herein.

The terms "machine readable medium" and "computer readable medium," as used herein, refer to any medium that participates in providing data that causes a machine to operate in a specific fashion. In an embodiment implemented using the computer system 1300, various computer readable media might be involved in providing instructions or code to the one or more processors 1310 for execution, might be used to store and/or carry such instructions/code such as signals, or both. In many implementations, a computer readable medium is a non-transitory, physical, or tangible storage medium. Such a medium may take many forms, including, but not limited to, non-volatile media, volatile media, and transmission media. Non-volatile media includes, for example, optical disks, magnetic disks, or both, such as the storage devices 1325. Volatile media includes, without limitation, dynamic memory, such as the working memory 1335. Transmission media includes, without limitation, coaxial cables, copper wire and fiber optics, including the wires that comprise the bus 1305, as well as the various components of the communication subsystem 1330, or the media by which the communications subsystem 1330 provides communication with other devices. Hence, transmission media can also take the form of waves, including without limitation radio, acoustic, or light waves, such as those generated during radio-wave and infra-red data communications.

Common forms of physical or tangible computer readable media include, for example, a floppy disk, a flexible disk, a hard disk, magnetic tape, or any other magnetic medium; a CD-ROM, DVD-ROM, or any other optical medium; punch cards, paper tape, or any other physical medium with patterns of holes; a RAM, a PROM, an EPROM, a FLASH-EPROM, or any other memory chip or cartridge; a carrier wave; or any other medium from which a computer can read instructions or code.

While certain features and aspects have been described with respect to exemplary embodiments, one skilled in the art will recognize that numerous modifications are possible. For example, the methods and processes described herein may be implemented using hardware components, software components, and/or any combination thereof. Further, while various methods and processes described herein may be described with respect to particular structural and/or functional components for ease of description, methods provided by various embodiments are not limited to any particular structural and/or functional architecture but instead can be implemented on any suitable hardware, firmware and/or software configuration. Similarly, while certain functionality is ascribed to certain system components, unless the context dictates otherwise, this functionality can be distributed among various other system components in accordance with the several embodiments.

Moreover, while the procedures of the methods and processes described herein are described in a particular order for ease of description, unless the context dictates otherwise, various procedures may be reordered, added, and/or omitted in accordance with various embodiments. Moreover, the procedures described with respect to one method or process may be incorporated within other described methods or processes; likewise, system components described according to a particular structural architecture and/or with respect to one system may be organized in alternative structural architectures and/or incorporated within other described systems. Hence, while various embodiments are described with—or without—certain features for ease of description and to illustrate exemplary aspects of those embodiments, the various components and/or features described herein with respect to a particular embodiment can be substituted, added and/or subtracted from among other described embodiments, unless the context dictates otherwise. Consequently, although several exemplary embodiments are described above, it will be appreciated that the invention is intended to cover all modifications and equivalents within the scope of the following claims.

What is claimed is:

1. A method of capturing an ophthalmic image comprising:
    providing an ophthalmic lens having an ophthalmic lens frame;
    providing an imaging device having an image sensor;
    providing a processor in communication with the imaging device;
    manually aligning the ophthalmic lens and imaging device with a patient eye causing an image of a selected structure of the patient eye and an image of the ophthalmic lens frame to be focused on the image sensor;
    obtaining a video stream of image data with the imaging device;
    detecting within the image data, with the processor, data corresponding to the ophthalmic lens frame;
    detecting, with the processor, image data indicating that a portion of an eye care specialist's finger has obstructed a portion of the ophthalmic lens frame; and
    upon detecting with the processor data indicating that a portion of an eye care specialist's finger has obstructed a portion of the ophthalmic lens frame, triggering, with the processor, the capture of a still frame image with the imaging device.

2. The method of claim 1, wherein the step of detecting with the processor image data indicating that a portion of the eye care specialist's finger has obstructed a portion of the ophthalmic lens frame comprises:
    determining an average color or intensity of the detected ophthalmic lens frame within the image data;
    determining a number of pixels within the boundaries of the detected ophthalmic lens frame that show a select color or intensity variance from the average color or intensity of the detected ophthalmic lens frame; and
    determining that a portion of the eye care specialist's finger has obstructed a portion of the ophthalmic lens frame when the number of pixels within the boundaries of the detected ophthalmic lens frame that show a select color or intensity variance from the average color or intensity of the detected ophthalmic lens frame exceeds a pre-determined threshold value.

3. The method of claim 1, wherein the step of detecting with the processor that a portion of the eye care specialist's finger has obstructed a portion of the ophthalmic lens frame comprises:
    detecting, with the processor, a pre-determined portion of ophthalmic lens frame in the image data; and
    detecting, with the processor, that a portion of an eye care specialist's finger has obstructed the pre-determined portion of the ophthalmic lens frame.

4. The method of claim 1, further comprising:
    determining, with the processor, the size and location on the still frame image of an interior edge of the ophthalmic lens frame; and
    cropping the captured still image to remove image data outside of the interior edge of the ophthalmic lens frame.

5. The method of claim 4, further comprising applying a solid color to the cropped portions of the still frame image.

6. The method of claim 1, further comprising connecting the ophthalmic lens frame to the imaging device with an adapter.

7. An ophthalmic imaging system comprising:
    an imaging device comprising a camera lens, an illumination source, an imaging sensor and imaging electronics;
    a processor in communication with the imaging device an ophthalmic lens comprising an ophthalmic lens frame; and
    one or more non-transitory computer readable media in communication with the processor having software stored thereon comprising a set of instructions that, when executed by the processor, causes the system to perform one or more functions, the set of instructions comprising:
        instructions to obtain a video stream of image data with the imaging device;
        instructions to detect, within the image data, data corresponding to the ophthalmic lens frame;
        instructions to detect, image data indicating that a portion of an eye care specialist's finger has obstructed a portion of the ophthalmic lens frame; and
        upon detecting with the processor data indicating that a portion of an eye care specialist's finger has obstructed a portion of the ophthalmic lens frame, instructions to trigger the capture of a still frame image with the imaging device.

8. The system of claim 7, wherein the set of instructions further comprise:
    instructions to determine an average color or intensity of the detected ophthalmic lens frame within the image data;
    instructions to determine a number of pixels within the boundaries of the detected ophthalmic lens frame that show a select color or intensity variance from the average color or intensity of the detected ophthalmic lens frame; and
    instructions to determine that a portion of the eye care specialist's finger has obstructed a portion of the ophthalmic lens frame when the number of pixels within the boundaries of the detected ophthalmic lens frame that show a select color or intensity variance from the average color or intensity of the detected ophthalmic lens frame exceeds a pre-determined threshold value.

9. The system of claim 7, wherein the set of instructions further comprise:
    instruction to detect a pre-determined portion of ophthalmic lens frame in the image data; and
    instructions to detect that a portion of an eye care specialist's finger has obstructed the pre-determined portion of the ophthalmic lens frame.

10. The system of claim 7, wherein the set of instructions further comprise:

instructions to determine the size and location on the still frame image of an interior edge of the ophthalmic lens frame; and instructions to crop the captured still image to remove image data outside of the interior edge of the ophthalmic lens frame.

11. The system of claim 10, wherein the set of instructions further comprise instructions to apply a select solid color to the cropped portions of the captured still image.

12. The system of claim 7, further comprising an adapter connecting the ophthalmic lens frame to the imaging device.

* * * * *